United States Patent [19]
Yoshihara et al.

[11] Patent Number: 5,102,655
[45] Date of Patent: Apr. 7, 1992

[54] HAIR TREATMENT COMPOSITION

[75] Inventors: Toru Yoshihara, Tokyo; Takahiro Kobayashi, Koshigaya; Tsutomu Muraoka, Tokyo, all of Japan

[73] Assignee: Kao Corporation, Tokyo, Japan

[21] Appl. No.: 482,858

[22] Filed: Feb. 22, 1990

[30] Foreign Application Priority Data

Feb 23, 1989 [JP] Japan ................. 1-44649

[51] Int. Cl.$^5$ .............. A61K 7/09; A61K 7/13; A61K 7/135
[52] U.S. Cl. ..................... 424/62; 424/72; 424/70; 8/405; 8/426; 8/405
[58] Field of Search .......... 424/62, 70, 72; 8/405, 8/406, 426, 606, 901, 916

[56] References Cited

U.S. PATENT DOCUMENTS 4,402,700 9/1983 Feinland et al. ............ 424/70 X
4,711,776 12/1987 Suzuki et al. ............... 424/70

FOREIGN PATENT DOCUMENTS 130609 1/1985 European Pat. Off.
181547 5/1986 European Pat. Off.
312343 4/1989 European Pat. Off.
2206045 12/1988 United Kingdom.

OTHER PUBLICATIONS

"Properties of Quaternary Ammonium Salts—Their Use in Cosmetic and Hair Treatment Preparations", Kluge, American Perfumer and Cosmetics, vol. 81, Mar. 1966, pp. 35-40.

Primary Examiner—Thurman K. Page
Assistant Examiner—Susan S. Rucker
Attorney, Agent, or Firm—Oblon, Spivak, McClelland, Maier & Neustadt

[57] ABSTRACT

A hair treatment composition is disclosed. The composition comprises: (A) a branched-type quaternary ammonium salt, (B) one or more agents selected from the group consisting of oxidizing agents, reducing agents, and dyeing agents, and (C) a higher alcohol having a branched ratio of 1-50%. The composition is directed to hair perming, hair dyeing, and the like, and exhibits excellent hair protecting and hair conditioning effects even under severe conditions. It features good handling performance, e.g. the capability of preventing running of the liquid and of providing superior spreadability. The excellent conditioning effect lasts for a long period of time even after repeated washing.

1 Claim, No Drawings

HAIR TREATMENT COMPOSITION

BACKGROUND OF THE INVENTION

1. Field of the Invention

This invention relates to a hair treatment composition such as a perming composition, a hair dye composition, and the like, and, more particularly, to a hair treatment composition which can prevent damage to the hair and provide an excellent conditioning effect.

2. Description of the Background Art

Perming compositions, hair dye compositions, and the like contain an oxidizing agent, reducing agent, or dyeing agent depending on their purpose of use. These agents, however, cause a great deal of damage to the cuticle of the hair. This, in turn, damages and roughens hair, and produces split and cut hair.

In order to overcome this problem, Japanese Patent Laid-open No. 96749/1977 proposes a hair dye composition comprising an oxidizing agent and a specific type of quaternary amine compound, and Japanese Patent Laid-open No. 49340/1979 proposes a hair dye composition comprising a fatty acid, an alkaline agent, and a specific type of cationic polymer. Both compositions, however, could not provide a long-lasting satisfactory conditioning effect.

Since hair treatment compositions such as perming compositions and hair dye compositions contain as their essential components an oxidizing agent, reducing agent, dyeing agent, or the like which imparts strong irritation to the skin, running of the treatment compositions down from the hair and adherence to the skin must be avoided. For this reason various types of thickeners to be added to such a hair treatment agent have been proposed and studied. The addition of a large amount of oily components or surface active agents, however, results in deterioration in spreadability and feeling to the touch. If oily components are reduced in order to decrease the viscosity, the composition is fluidified and tends to run down, which means cumbersome handling.

In view of this situation, the inventors of the present invention have carried out extensive studies, and, as a result, have discovered that the above problems in conventional hair treatment compositions could be overcome by the addition of a branched-type quaternary ammonium salt and a higher alcohol having a branched ratio of 1-50%. Such findings have led to the completion of the present invention.

SUMMARY OF THE INVENTION

Accordingly, an object of this invention is to provide a hair treatment composition comprising: (A) a branched-type quaternary ammonium salt, (B) one or more agents selected from the group consisting of oxidizing agents, reducing agents, and dyeing agents, and (C) a higher alcohol having a branched ratio of 1-50%.

Another object of this invention is to provide a hair treatment composition comprising: (A) a branched-type quaternary ammonium salt, (D) an anionic polymer, and (B) one or more agents selected from the group consisting of oxidizing agents, reducing agents, and dyeing agents.

Other objects, features and advantages of the invention will hereinafter become more readily apparent from the following description.

DETAILED DESCRIPTION OF THE INVENTION AND PREFERRED EMBODIMENTS

Excellent hair protecting and hair conditioning effects, even under severe conditions, can be obtained by the combined use of components (A), (B), and (C). Such effects could not be obtained by the use of conventional mono- or dialkyl ammonium salts. Furthermore, liquid crystals produced by the combination of components (A) and (C) prevent the composition from running down and make it readily spreadable upon application of a stress.

Branched quaternary ammonium salts which can be used as component (A) of the present invention include those represented by following general formula (I) or (II),

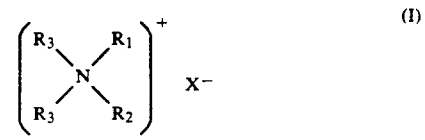

in which $R_1$ and $R_2$ individually represent an alkyl group having 1-3 carbon atoms, a hydroxyalkyl group having 1-3 carbon atoms, or a benzyl group, two $R_3$s independently represent a mixture of (a) a branched alkyl group of the formula

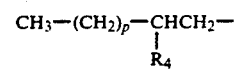

and (b) a linear alkyl group of the formula $CH_3-(CH_2)_q-$, wherein $R_4$ represents a methyl or ethyl group, p and q is an integer to make the carbon atom content of alkyl group (a) or (b) 8 to 16, with a ratio $(a)/[(a)+(b)]$ being 10-100% by weight, and X represents a halogen ion or an organic anion.

Branched quaternary ammonium salts represented by general formula (I) are produced, for example, from oxo alcohols having an 8 to 16 carbon atom content. Specific examples are dialkyldimethylammonium salt, dialkylmethylhydroxyethylammonium salt, or dialkylmethylbenzylammonium salt, all having an alkyl group derived from an oxo alcohol. Counter ions for these ammonium salts may be a halogen ion such as chlorine ion, bromine ion, or iodine ion, or an organic anion such as methosulfate, ethosulfate, methophosphate, ethophosphate, or the like.

The alkyl group, $R_3$ in formula (I), is a group comprised of (a) a group represented by

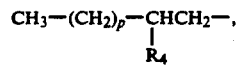

wherein $R_4$ represents a methyl or ethyl group, and (b) a group represented by $CH_3-(CH_2)_q-$, both having an 8 to 16 carbon atom content. The "branched ratio" for $R_3$, $(a)/[(a)+(b)]$, is usually in the range of 10-100% by weight, and particularly preferably in the range of 10-50% by weight. Although the total carbon number of the alkyl group $R_3$ may be 8 to 16, preferable groups are those having a certain distribution of the carbon atom content. An especially preferable carbon number distribution is as follows.

- $C_8$–$C_{11}$: less than 5% by weight
- $C_{12}$: 10–35% by weight
- $C_{13}$: 15–40% by weight
- $C_{14}$: 20–45% by weight
- $C_{15}$: 5–30% by weight
- $C_{16}$: less than 5% by weight Specific examples of particularly preferable branched quaternary ammonium salts represented by formula (I) are dialkyldimethylammonium chloride in which the alkyl group $R_3$ has 8 to 16 carbon atoms and a branched ratio is 10–50% by weight.

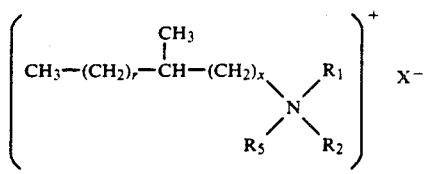
(II)

wherein r is an integer of 2–14, x is an integer of 3–11, provided that the sum of r and x is 9–21, $R_5$ is a group, (c):

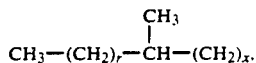

or an alkyl group having 1–3 carbon atoms, and $R_1$, $R_2$, and X have the same meanings as defined for formula (I).

For methyl branched quaternary ammonium salts of formula (II), those having the sum r and x of 15 are preferable. Examples are isostearyltrimethylammonium chloride, isostearyldimethylammonium chloride, and the like.

These branched-type quaternary ammonium salts can be used independently or two or more of them can be used as a mixture. The amount to be added to the hair treatment composition is 0.01–10% by weight, and preferably 0.03–5% by weight.

Any oxidizing agents, reducing agents, and dyeing agents which are commonly used for perming or hair dye compositions can be used without limitation as a component (B). Given as examples of oxidizing agents are hydrogen peroxide, sodium persulfate, ammonium persulfate, sodium perborate, urea peroxide, sodium percarbonate, sodium tripolyperphosphate, sodium bromate, potassium bromate, sodium pyroperphosphate, sodium orthoperphosphate, sodium silicate-hydrogenperoxide adduct, and the like. The amount to be added to the hair treatment composition is about 0.1–10% by weight. Reducing agents which can be used include thioglycolic acid, cystein, sulfite, and the like. The amount to be added to the composition of the present invention is 0.05–10% by weight.

Hair dye components can be broadly grouped into the oxidation-type (permanent type), the non-oxidation-type (permanent- and semi-permanent-type), and the non-oxidation-type (temporary type). In the oxidation-type hair dye compositions, a dye intermediate is oxidized by an oxidizing agent to produce a coloring substance. The coloring substance dyes the hair. A coupler does not produce color itself by oxidation, although it can produce a color when oxidized in the presence of dye intermediates. The oxidizing-type hair dye compositions, therefore, contain a dye intermediate, an oxidizing agent, and, if necessary, couplers. Among these, commonly used dye intermediates are para- or ortho compounds such as p-phenylenediamine, toluene-2,5-diamine, N-phenyl-p-phenylenediamine, 4,4'-diaminodiphenylamine, p-aminophenol, p-methylaminophenol, o-phenylenediamine, toluene-3,4-diamine, o-aminophenol, p-chloro-o-phenylene-diamine, p-amino-o-cresol, o-chloro-p-phenylenediamine, fluoroglucin, pyrrogarol, 3,3'-iminodiphenol, diphenylamine, 2,6-diaminopyridine, p-aminophenylsulfamine, and the like; commonly used couplers are metha components or phenols such as m-phenylenediamine, toluene-2,4-diamine, p-methoxy-m-phenylenediamine, m-aminophenol, α-naphthol, resorcinol, hydroquinone, catechol, and the like. In addition to the above components, the oxidation-type hair dye compositions may contain non-oxidation dyes which affect the color tone of the hair without being involved in the color forming reaction. Such compounds, which promote the utility of dye compositions include nitro dyes such as nitro-p-phenylenediamine, p-nitro-o-phenylenediamine, 2-amino-4-nitrophenol, 2-amino-5-nitrophenol, and 4-amino-2-nitrophenol; and direct dyes such as picramic acid, picric acid, and 1,4-diaminoanthraquinone; and the like.

Typical permanent or semi-permanent non-oxidation-type hair dyes are hair dyes of plant origin and of metallic hair dyes. Hair dyes of plant origin contain an extract of henna, walnut, soybean, or the like as their hair-dyeing base components. Color elements in the plant extracts exercise a dyeing action on hair keratin. Metallic hair dyes utilize a reaction of metals for producing insoluble metallic salts. Iron, copper, lead, manganese, nickel, cadmium, and the like are preferable metals for use as metallic hair dye base components. Especially preferable compounds are iron salts.

In the case of temporary non-oxidation-type hair dyes, hair dyeing base components such as acid dyes and pigments, and the like are directly adhered to the hair, or a resin containing these components is coated onto the hair. There are no specific limitations as to the dyes or pigments. For example, pigments such as titanium oxide and carbon black; coloring agents derived from coal tar such as triphenylmethane dye, azo dye, quinoline dye, xanthene dye, acridine dye, azine dye, oxazine dye, indigoid dye, anthraquinone dye, stilbene dye, and thiazole dye; and the like can be used.

The dye agents, as component (B), are added to the composition in the amount of 0.1–5% by weight.

Component (C), a higher alcohol having a branched ratio of 1–50%, can be prepared by mixing linear higher alcohols and branched higher alcohols. Linear higher alcohols having 12–24 carbon atoms are preferable. Specific examples are lauryl alcohol, myristyl alcohol, cetyl alcohol, stearyl alcohol, behenyl alcohol, and the like. Branched higher alcohols which can be used include iso-branched alcohols, poly-branched alcohols, Guerbet-branched alcohols, monomethyl branched alcohols, and the like. Iso-branched alcohols are the branched alcohols obtained by the oxo reaction of α-olefin. Their chain length and branched ratios vary depending on the reaction conditions. Specific examples of iso-branched alcohols include Dovanol 23 (trademark: manufactured by Mitsubishi Petrochemical Co., Ltd.) having a chain length of $C_{12}$–$C_{13}$ and the branched ratio of 20–30%), Dovanol 45 (trademark: manufactured by Mitsubishi Petrochemical Co., Ltd.)

having a chain length of $C_{13}-C_{15}$ and a branched ratio of 20-30%), Dovanol 23i (trademark: manufactured by Mitsubishi Petrochemical Co., Ltd.) having a chain length of $C_{12}-C_{13}$ and the branched ratio of 93%), and Oxo Alcohol 710 (trademark: manufactured by Nissan Chemical Co., Ltd.) having a chain length of $C_7-C_{10}$). Poly-branched alcohols are the alcohols having methyl branches and 7-13 carbon atoms. They are prepared by the oxo reaction of α-olefin which is obtained by dimerization, trimerization, or tetramerization of 1-propylene. Their branched ratio is 100%. Specific examples are Nissan Heptanol, Nissan Decanol, and Nissan Tridecanol, all of which are trademarks and manufactured by Nissan Chemical Co., Ltd. Nissan Nonanol and Fine Oxo Alcohol 180, both of which are trademarks and manufactured by Nissan Chemical Co., Ltd., derived from 2,4,4-trimethylpentene can also be given as examples.

Guerbet alcohols are branched higher alcohols prepared by dimerization of higher alcohols by the Guerbet method. They have the formula,

(III)

wherein $R_6$ and $R_7$ individually represent an alkyl group having 2-16, preferably 12-16, carbon atoms. Specific examples include 2-hexyldecanol (e.g. Enujecol 160A: trademark, manufactured by Shin-Nippon Rika Co., Ltd.), 2-heptylundecanol (Diadol 18G: trademark, manufactured by Mitsubishi Chemical Co., Ltd.), 2-octyldodecanol (e.g. Enujecol 200A: trademark, manufactured by Shin-Nippon Rika Co., Ltd.), 2-decyltetradecanol (e.g. Enujecol 240A: trademark, manufactured by Shin-Nippon Rika Co., Ltd.), 2-dodecylhexadecanol, and the like. Monomethyl-branched-type higher alcohols are the branched higher alcohols prepared by the esterification of monomethyl-branched-type fatty acids of the formula,

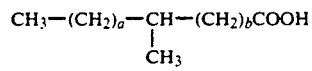

wherein a is an integer of 2-14 and b is an integer of 2-10, provided that the sum of a and b is 8-20 (e.g. #875: trademark, manufactured by Emery Corp.; Prizoline: trademark, manufactured by Unichema Co.), followed by hydrogenation of the ester.

Any of the above branched higher alcohols can be used, although preferable alcohols are Guerbet-type alcohols.

The branched higher alcohols are added to the composition of the present invention in an amount of 1-20% by weight, preferably 3-15% by weight, as component (C).

The hair treatment composition of the present invention exhibits an excellent conditioning effect on the hair. Since the composition forms a liquid crystal-emulsion state, it has a suitable viscosity. Due to this property, the composition does not run down and exhibits splendid spreadability when a stress is applied.

In a preferred embodiment of the hair treatment composition which comprises components (A), (B), and (C), a linear mono-alkyl quaternary ammonium salt having 12-28, preferably 16-24, carbon atoms can be added in an amount of 1-10% by weight in addition to these three components in order to improve the emulsion stability. Such a linear mono-alkyl quaternary ammonium salt may be cetyltrimethylammonium chloride, stearyltrimethylammonium chloride, behenyltrimethylammonium chloride, and the like.

Furthermore, when the branched quaternary ammonium salt, component (A), is used in combination with an anionic polymer, the hair treatment composition exhibits an excellent conditioning effect for a long period of time, even if the hair is repeatedly washed.

Accordingly the present invention provides, as another embodiment of the present invention, a hair treatment composition comprising: (A) a branched-type quaternary ammonium salt, (D) an anionic polymer, and (B) one or more agents selected from the group consisting of oxidizing agents, reducing agents, and dyeing agents.

The following compounds are given as examples of anionic polymers used as component (D).

(1) Natural polymers

They are extracted from natural substances. Examples include polysacchairdes, e.g. xanthan gum, pectin, carageenan; cellulose, e.g. carboxymethyl cellulose; and the like. Given as examples of commercially available polymers are Keltrol (trademark, manufactured by Kerco Co.), Apple Pectin (trademark, manufactured by Helpshlight Co.), Aqualon (trademark, manufactured by Nitta Geratin Co., Ltd.), and the like.

(2) Acidic vinylether polymers

Examples are partial lower alkyl esters of copolymers formed by methyl vinyl ether and maleic anhydride, and the like. Gantlez ES-225 and Gantlez ES-335 (trademarks, manufactured by Guf Co.) and the like are given as commercially available products (3) Acidic polyvinyl acetate polymers These are typified by copolymers of vinyl acetate and crotonic acid and, as commercial products, Resin 28-1310 and Resin 28-2930 (trademarks, manufactured by National Starch Co.) and Luviset CE5055 (trademark, manufactured by Yuka Badish Co., Ltd.).

(4) Acidic acrylic polymers

They are, for example, copolymers of methacrylic acid and alkyl methacrylate, copolymers of acrylic acid, alkyl acrylate, and N-alkylacrylamide, copolymers of acrylic acid and polyhydric alcohol, e.g. allyl sugar (a typical example of the last-mentioned copolymer is carboxyvinyl polymer). Plascize (trademark, manufactured by Goou Chemical Co., Ltd.), Ultrahold 8 (trademark, manufactured by Ciba Gaigee), Carbopol 941 (trademark, manufactured by B. F. Goodrich Chemical Co.), and the like are as examples of commercially available the acidic acrylic polymers.

Particularly preferable polymers among the above-mentioned examples are xanthan gum, pectin, carageenan, carboxymethyl cellulose, acidic acrylic polymers. Component (D) is added to an amount of 0.001-5%, preferably 0.003-2% by weight of the total weight of the hair treatment composition.

To the hair treatment compositions of the types illustrated above, i.e., one type comprising components (A), (B), and (C), and another comprising components (A), (B), and (D), added are, in addition to these essential components, optional components such as nonionic surfactants, e.g. POE alkyl ether, POE alkylphenyl ether; oil components, e.g. silicone, liquid paraffin; solvents, e.g. propylene glycol, glycerol; and the like to the extent that the effects of the present invention are not adversary affected. In addition, alkaline agents, stabilizers, anti-oxidants, preservatives, perfumes, and the like which are commonly used for hair dye or perming compositions can also be used together.

The hair treatment composition of the present invention exhibits excellent hair protecting and hair conditioning effects even under severe conditions. In addition, it features good handling performance including the capability of preventing running of the liquid and of providing superior spreadability. Since the excellent conditioning effect lasts for a long period of time even after repeated washing, the hair can be effectively protected from one perming or dyeing treatment through the next treatment.

Other features of the invention will become apparent in the course of the following description of the exemplary embodiments which are given for illustration of the invention and are not intended to be limiting thereof.

EXAMPLES

Example 1

Hair dye compositions, Comparative Products 1-3 and Example Products 1-3 were prepared. The first reagent of each product had the formulation given in Table 1.

TABLE 1

| Component | Comparative Product | | | Example Product | | |
|---|---|---|---|---|---|---|
| | 1 | 2 | 3 | 1 | 2 | 3 |
| (1) p-Phenylenediamine | 2.0 | 2.0 | 2.0 | 2.0 | 2.0 | 2.0 |
| (2) o-Aminophenol | 1.0 | 1.0 | 1.0 | 1.0 | 1.0 | 1.0 |
| (3) m-Phenylenediamine | 0.2 | 0.2 | 0.2 | 0.2 | 0.2 | 0.2 |
| (4) Stearyltrimethylammonium chloride | 3.0 | — | — | — | — | — |
| (5) Distearyltrimethylammonium chloride | 1.0 | — | — | — | — | — |
| (6) Dialkyldimethylammonium chloride (*1) | — | 4.0 | 4.0 | 4.0 | 4.0 | — |
| (7) Iso-stearyltrimethylammonium chloride | — | — | — | — | — | 4.0 |
| (8) Cetostearyl alcohol | 6.0 | 6.0 | 0.4 | 6.0 | 6.0 | 6.0 |
| (9) 2-Hexyldecanol (*2) | — | — | 6.0 | 0.4 | — | 0.4 |
| (10) 2-Dodecylhexadecanol (*3) | — | — | — | — | 0.4 | — |
| (11) Sodium sulfite | 0.1 | 0.1 | 0.1 | 0.1 | 0.1 | 0.1 |
| (12) Propylene glycol | 2.0 | 2.0 | 2.0 | 2.0 | 2.0 | 2.0 |
| (13) Aqueous ammonia | (The amount needed to make the product pH 10) | | | | | |
| (14) Water | (Balance) | | | | | |

(*1) Branched-type quaternary ammonium salt prepared from commercially available $C_{12}$-$C_{15}$ oxo alcohols [a mixture of an equivalent amount of Dovanol 23 and Dovanol 45 (trademarks: manufactured by Mitsubishi Petrochemical Co., Ltd.), having a branched ratio of 20% by weight.
(*2) Enujecol 160A (trademark, manufactured by Shin-Nippon Rika Co., Ltd.)
(*3) Synthesized by dimerization of $C_{14}H_{29}OH$ by the Garbet method followed by distillation.

The oxidant of the following formulation was used for all products.

| | (% by weight) |
|---|---|
| (1) Hydrogen peroxide | 6.0 |
| (2) POE (20) cetyl ether | 8.0 |
| (3) Cetostearyl alcohol | 8.0 |
| (4) Propylene glycol | 2.0 |
| (5) Liquid paraffin | 0.5 |
| (6) Phosphoric acid | (The amount needed to make the product pH 10) |
| (7) Water | (Balance) |

<Methods of Evaluation>
(1) Appearance
  The emulsions was observed by naked eye.
(2) Easiness of Application A mixture of an equal amount of the first reagent and the oxidant was applied to the hair, left for 30 minutes, and washed with water. This procedure was carried out and the evaluation was made by 5 expert panelists for each product.

The results are shown in Table 2.

TABLE 2

| | Appearance | Application performance | | Rinse out easiness |
|---|---|---|---|---|
| | | Run-down | Spreadability | |
| Comparative Product 1 | Crystals deposited | Nil | Poor | Product adhered to the hair and was hard to remove |
| Comparative Product 2 | Crystals deposited | Nil | Poor | Product adhered to the hair and was hard to remove |
| Comparative Product 3 | No crystal deposited | dropped | Good | Good |
| Invention Product 1 | No crystals deposited | Nil | Good | Good |
| Invention Product 2 | No crystals deposited | Nil | Good | Good |
| Invention Product 3 | No crystals deposited | Nil | Good | Good |

The invention Products 1 and 2 gave a good feeling to the touch; i.e., they gave an excellent smooth, soft, and moistened sensation.

Example 2

Example Product 4 was prepared according to the same formulation as Example Product 1, except for a further addition of 0.05% of Apple Pectin OM (trademark, manufactured by Helpshlight Co.). A hair sample was dyed with the Example Product 4 in the same manner as in Example 1.

As a result, the product was found to exhibit no cream run-down and to have good spreadability. It gave an excellent smooth, soft, and moistened sensation. The effects hardly changed after 7-times repeated treatment by 5% aqueous solution of sodium dodecylsulfate followed each time by washing with water.

Example 3

A creamy hair dye composition (Example Product 4) of the following formulation was prepared.

| <First reagent> | % by weight |
| --- | --- |
| (1) p-Phenylenediamine | 2.0 |
| (2) o-Aminophenol | 1.0 |
| (3) m-Phenylenediamine | 0.2 |
| (4) Stearyltrimethylammonium chloride | 2.5 |
| (5) Dialkyldimethylammonium chloride* | 1.5 |
| (6) POE (20) cetyl ether | 1.0 |
| (7) Cetostearyl alcohol | 6.0 |
| (8) 2-Hexyldecanol | 0.4 |
| (9) Propylene glycol | 5.0 |
| (10) Sodium sulfite | 0.1 |
| (11) Methyl paraben | 0.1 |
| (12) Aqueous ammonia | (The amount needed to make the product pH 10) |
| (13) Perfume | 0.3 |
| (14) Apple Pectin OM (Helpshlight Co.) | 0.05 |
| (15) Water | Balance |

*The same component as used for component (6) of Example Product 1.

The composition exhibited a moderate fluidity when blended with an oxidant without cream run-down. It spread very well so that it was easily applied to the object and rinsed out very efficiently. When applied to the hair sample, it exhibited a superior conditioning effect. The conditioning effect hardly changed by 7-times repeated shampoo treatment.

Example 4

A creamy hair dye composition (Comparative Product 4) of the following formulation was prepared.

| <First reagent> | % by weight |
| --- | --- |
| (1) p-Phenylenediamine | 2.0 |
| (2) o-Aminophenol | 1.0 |
| (3) m-Phenylenediamine | 0.2 |
| (4) Stearyltrimethylammonium chloride | 2.5 |
| (5) 2-Octyldodecyltrimethylammonium chloride | 1.5 |
| (6) POE (20) cetyl ether | 1.0 |
| (7) Cetostearyl alcohol | 6.0 |
| (8) 2-Hexyldecanol | 0.4 |
| (9) Propylene glycol | 5.0 |
| (10) Sodium sulfite | 0.1 |
| (11) Methyl paraben | 0.1 |
| (12) Aqueous ammonia | (The amount needed to make the product pH 10) |
| (13) Perfume | 0.3 |
| (14) Apple Pectin OM (Helpshlight Co.) | 0.05 |
| (15) Water | Balance |

Hair bundles taken from a Japanese, each weighing about 20 g, were dyed with Example Product 4 and Comparative Product 4. The dyed hair bundles were shampooed, washed with water, dried, and subjected to sensory evaluation by 10 women in terms of easiness of comb passage, smoothness, softness, and feeling to the touch. The results are shown in Table 3.

TABLE 3

|  | Example Product 4 was better | Comparative Product 4 was better | Could not tell which was better |
| --- | --- | --- | --- |
| Comb passage | 6 | 1 | 3 |
| Smoothness | 6 | 2 | 2 |
| Softness | 7 | 0 | 3 |
| Feeling to the touch | 7 | 1 | 2 |

Example 5

A creamy hair dye composition of the following formulation was prepared.

| <First reagent> | % by weight |
| --- | --- |
| (1) p-Phenylenediamine | 2.0 |
| (2) o-Aminophenol | 0.5 |
| (3) m-Phenylenediamine | 0.2 |
| (4) Resorcinol | 1.0 |
| (5) Stearyltrimethylammonium chloride | 2.0 |
| (6) Isostearyltrimethylammonium chloride | 1.0 |
| (7) POE (20) cetyl ether | 1.0 |
| (8) Cetostearyl alcohol | 6.0 |
| (9) 2-Heptylundecanol | 0.6 |
| (10) Propylene glycol | 5.0 |
| (11) Sodium sulfite | 0.1 |
| (12) Methyl paraben | 0.1 |
| (13) Aqueous ammonia | (The amount needed to make the product pH 10) |
| (14) Perfume | 0.3 |
| (15) Apple Pectin OM (Helpshlight Co.) | 0.1 |
| (16) Water | Balance |

The composition exhibited a moderate fluidity when blended with an oxidant without cream run-down. It spread very well so that it was easily applied to the object and rinsed out very efficiently. When applied to a hair sample, it exhibited a superior conditioning effect. The conditioning effect hardly changed by 7-times repeated shampoo treatment.

Example 6

A creamy hair bleaching composition of the following formulation was prepared.

| <First reagent> | % by weight |
| --- | --- |
| (1) Stearyltrimethylammonium chloride | 1.5 |
| (2) Dialkyldimethylammonium chloride* | 1.0 |
| (3) POE (23) lauryl ether | 5.0 |
| (4) Cetostearyl alcohol | 6.0 |
| (5) 2-Octyldodecanol | 0.5 |
| (6) Propylene glycol | 4.5 |
| (7) Methyl paraben | 0.1 |
| (8) Aqueous ammonia | (The amount needed to make the product pH 10) |
| (9) Xanthan gum (Kerco Co.) | 0.2 |
| (10) Water | Balance |

*The same component as used for component (6) of Example Product 1.

The composition exhibited a moderate fluidity when blended with an oxidant without cream run down. It spread very well so that it was easily applied to the object and rinsed out very efficiently. When applied to a hair sample, it exhibited a superior conditioning effect. The conditioning effect hardly changed by 7-times repeated shampoo treatment.

Example 7

A permanent wave composition of the following formulation was prepared.

|  | % by weight |
|---|---|
| <Waving lotion> | |
| (1) Thioglycolic acid | 6.0 |
| (2) Cetostearyl alcohol | 0.2 |
| (3) POE (20) cetyl ether | 0.7 |
| (4) Dialkyldimethylammonium chloride* | 0.2 |
| (5) Apple Pectin OM (Helpshlight Co.) | 0.05 |
| (6) Aqueous ammonia | (The amount needed to make the product pH 9) |
| (7) Water | Balance |
| <Fixing Lotion> | |
| (1) Sodium bromate | 10.0 |
| (2) Water | 90.0 |

*The same component as used for component (6) of Example Product 1.

The composition gave a superior conditioning effect, which lasted for 15 days.

Example 8

A creamy acid hair dye composition of the following formulation was prepared.

|  | % by weight |
|---|---|
| (1) Acid Red 18 | 0.3 |
| (2) Acid Yellow 23 | 0.1 |
| (3) Behenyltrimethylammonium chloride | 1.5 |
| (4) Dialkyldimethylammonium chloride* | 1.5 |
| (5) POE (20) cetyl ether | 1.0 |
| (6) Cetostearyl alcohol | 4.5 |
| (7) 2-Octyldodecanol | 0.3 |
| (8) Propylene glycol | 5.0 |
| (9) Citric acid | (The amount needed to make the product pH 3) |
| (10) Methyl paraben | 0.1 |
| (11) Perfume | 0.3 |
| (12) Water | Balance |

*The same component as used for component (6) of Example Product 1.

The acid hair dye composition exhibited a moderate fluidity without cream run-down. It spread very well so that it was easily applied to the object and rinsed out very efficiently. When applied to the hair sample, it exhibited a superior conditioning effect.

Example 9

A liquid hair dye composition of the following formulation was prepared.

|  | % by weight |
|---|---|
| <Color lotion> | |
| (1) p-Phenylenediamine | 2.0 |
| (2) o-Aminophenol | 1.0 |
| (3) m-Phenylenediamine | 0.2 |
| (4) Isostearyltrimethylammonium chloride | 1.0 |
| (5) POE (6) stearyl ether | 1.0 |
| (6) Apple Pectin OM (Helpshlight Co.) | 0.05 |
| (7) Propylene glycol | 10.0 |
| (8) Perfume | 0.3 |
| (9) Sodium sulfite | 0.1 |
| (10) Oleic acid | 8.0 |
| (11) Oleyl alcohol | 1.0 |
| (12) Aqueous ammonia | (The amount needed to make the product pH 10) |
| (13) Water | Balance |
| <Oxidant> | |
| (1) Hydrogen peroxide | 6.0 |
| (2) Water | 94.0 |

The composition exhibited a superior conditioning effect. The conditioning effect hardly changed by 7-time repeated shampoo treatment.

Obviously, numerous modifications and variations of the present invention are possible in light of the above teachings. It is therefore to be understood that within the scope of the appended claims, the invention may be practiced otherwise than as specifically described herein.

What is claimed is:

1. A hair treatment composition comprising:

(A) a quaternary ammonium salt selected from a group of compounds represented by the following formulae (I) and (II),

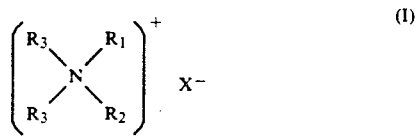

wherein $R_1$ and $R_2$ individually represent an alkyl group having 1-3 carbon atoms, a hydroxyalkyl group having 1-3 carbon atoms, or a benzyl group, two $R_3$s independently represent a mixture of (a) a branched alkyl group of the formula

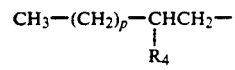

and (b) a linear alkyl group of the formula $CH_3-(CH_2)_q-$, wherein $R_4$ represents a methyl or ethyl group, p and q is an integer to make the carbon atom content of the alkyl group (a) or (b) 8 to 16, with a ratio (a)/((a)+(b)) being 10–100% by weight, and X represents a halogen ion or an organic anion, and

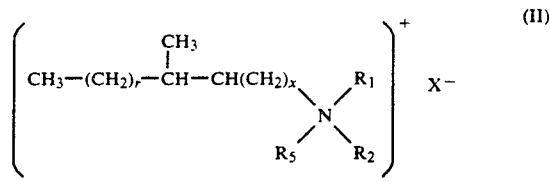

wherein r is an integer of 2-14, x is an integer of 3-11, provided that r plus x is 9-21, $R_5$ is a group, (c):

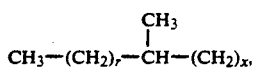

or an alkyl group having 1-3 carbon atoms, and $R_1$, $R_2$, and x have the same meanings as defined for formula (I):

(B) one or more agents selected from the group consisting of oxidizing agents, reducing agents and dyeing agents; and (C) a mixture of linear higher alcohols and branched higher alcohols, said mixture containing 1-50% of said branched higher alcohols, said branched higher alcohols being selected from the group consisting of iso-branched alcohols and Guerbet alcohols.

* * * * *